United States Patent [19]
Horwitz

[11] Patent Number: 5,756,547
[45] Date of Patent: May 26, 1998

[54] METHOD FOR THE TREATMENT OF PRESERVING ORGANS OR TISSUE FOR TRANSPLANTATION

[75] Inventor: Lawrence D. Horwitz, Englewood, Colo.

[73] Assignee: Regents of the University of Colorado, Boulder, Colo.

[21] Appl. No.: 862,534

[22] Filed: May 23, 1997

Related U.S. Application Data

[62] Division of Ser. No. 598,926, Feb. 9, 1996, Pat. No. 5,670,545.

[51] Int. Cl.$^6$ ......................... A61K 31/16; A61K 31/165
[52] U.S. Cl. ............................................. 514/613; 514/618
[58] Field of Search ..................................... 514/613, 618

[56] References Cited

U.S. PATENT DOCUMENTS 4,305,958 12/1981 Fujita et al. .............................. 424/319

*Primary Examiner*—Kimberly Jordan
*Attorney, Agent, or Firm*—Greenlee, Winner & Sullivan, P.C.

[57] ABSTRACT

Bucillamine and N-2,2-dimethyl-3-mercaptopropionyl)-L-cysteine or related compounds can be used to prevent damage to living tissue from the formation or presence of reactive oxygen species. These reactive oxygen species are formed when tissue is first rendered hypoxic due to interruption of blood flow and then reoxygenated by restoration of blood flow. In particular, the invention is directed to the administration of bucillamine and N-2,2-dimethyl-3-mercaptopropionyl)-L-cysteine prior to or coincidental with reperfusion to prevent damage to myocardium from formation of reactive oxygen species. Also presented are application of these compounds to similar ischemia-related cell injury in other organs.

12 Claims, 2 Drawing Sheets

METHOD FOR THE TREATMENT OF PRESERVING ORGANS OR TISSUE FOR TRANSPLANTATION

CROSS-REFERENCE TO RELATED APPLICATIONS

This application is a division of U.S. patent application Ser. No. 08/598,926, filed Feb. 9, 1996, now U.S. Pat. No. 5,670,545, which is incorporated in its entirety by reference herein

FIELD OF THE INVENTION

The present invention relates to a method for the treatment of ischemic diseases using N-mercaptoalkanoylcysteine compounds. These compounds also protect tissue from the adverse effects of reactive oxygen species.

BACKGROUND OF THE INVENTION

In acute myocardial infarction, cardiac tissue is damaged by two sequential events, hypoxia in the ischemic phase and oxidative damage in the reperfusion phase. Damaged cardiac tissue in the ischemic phase can be salvaged by restoring blood flow to the ischemic region through reperfusion. However, restoration of blood containing oxygen can result in injury due to the production of reactive oxygen species [Biochim. Biophys. Acta, 890:82–88 (1987)]. Two of these reactive oxygen species, hydrogen peroxide and superoxide radical, are thought to be of particular importance in causing injury to myocardial cells exposed to ischemia and reperfusion [Free Radical Res. Commun. 9:223–232 (1990); Basic Res. Cardiol. 84:191–196 (1989)]. Injury from hydrogen peroxide and superoxide radicals occurs when in the presence of iron there is generation of highly toxic hydroxyl radicals [Am. J. Physiol. (1994) 266:H121–H127]. Hydroxyl radicals can also be produced from the simultaneous generation of superoxide radical and nitric oxide, and this reaction could also cause tissue injury ([Biochemical J. 281:419–424 (1992)]. If hydrogen peroxide, superoxide radical, or other reactive oxygen species accumulate during the reperfusion phase, various toxic reactions can occur which result in myocardial cell injury or death. Similar injury to heart tissue can occur during heart surgery when bypass procedures or other manipulations result in an ischemic phase followed by a reperfusion phase. Similar injury to other organs such as the brain, kidney or intestine can also occur due to ischemia and reperfusion and production of reactive oxygen species [J. Appl. Physiol. 71:1185–1195 (1991); Kidney Int. 40:1041–1049 (1991)]. Injury due to generation of reactive oxygen species, probably resulting from exposure to ischemia and reperfusion, also occurs during transplantation of organs such as hearts, kidneys, livers or lungs [J. Thorax. Cardiovasc. Surgery (1992) 103:945–951; Clinical Transplantation (1995) 9:171–175]. In addition, injury due to reactive oxygen species to the coronary arteries or other blood vessels can occur either due to exposure to ischemia and reperfusion [Am. J. Physiol. 260:H42–H49 (1990)] or under other conditions when they may contribute to atherosclerosis [Proc. Natl. Acad. Sci. U.S.A. 84:2995–2998 (1987)]. Although ischemia followed by reperfusion is the usual cause of production of reactive oxygen species in the myocardium and blood vessels, there may be accumulation of reactive oxygen species in these organs from other mechanisms. For example, the accumulation of reactive oxygen species has been implicated in heart failure [Free Radical Biology Med. 14:643–647 (1993)]. Production of superoxide radical or other reactive oxygen species in vascular tissue can cause tolerance to certain drugs used for treatment of heart disease, such as nitroglycerin and related nitrates [J. Clin. Invest. 95:187–194 (1995)].

There is a need for methods of treatment of ischemia and reperfusion which avoid the problems in prior art methods. More specifically, there is a need for improved methods of reperfusion in which the effects of reactive oxygen species are neutralized. This invention provides N-mercaptoalkanoylcysteine compounds that ameliorate or prevent the toxic effects of reactive oxygen species, including but not limited to hydrogen peroxide and superoxide radical, without themselves damaging tissue.

N-mercaptoalkanoylcysteine derivatives have been reported to be useful for a variety of pharmaceutical applications, for example for the treatment of hepatic diseases and autoimmune diseases such as rheumatoid arthritis (see Laid-Open Japanese Patent Application No. 2–776).

The N-mercaptoalkanoylcysteine, bucillamine (N-(2-methyl-2-mercaptopropionyl)-L-cysteine, also designated 2-mercaptoisobutyroyl-1-cysteine) (See: U.S. Pat. No. 4,305,958) which has formula:

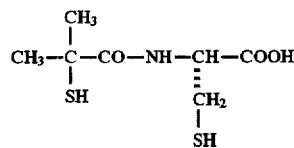

is reported useful in a variety of pharmaceutical applications: as a dissolving agent for sputum (see Laid-Open Japanese Patent Application No. 53-5112), an antirheumatic agent (see Laid-Open Japanese Patent Application No. 55-51020), a treatment for cataracts (see Laid-Open Japanese Patent Application No. 55-92315, a treatment for diabetes (see Laid-Open Japanese Patent Application No. 4-154721), and a treatment for osteoporosis (see Laid-Open Japanese Patent Application No. 4-154722). Its homolog N-2,2-dimethyl-3-mercaptopropionyl)-L-cysteine (See: U.S. Pat. No. 5,292,926), hereafter Compound A, of formula:

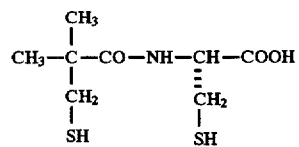

is reported useful for treatment of cataracts (see Laid-Open Japanese Patent Application No. 6-56661). None of these reports of therapeutic applications of bucillamine, Compound A or other N-mercaptoalkanoylcysteines teaches or suggests the use of these compounds to prevent or treat reperfusion injury.

2-Mercaptopropionylglycine (MPG) of formula:

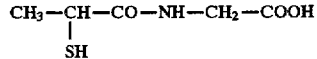

and related compounds, including bucillamine (but not Compound A) were tested for their ability to treat mitochondrial dysfunction and postischemic myocardial damage (Arzneim-Forschung Drug Research (1985) 35:1394–1402). This reference suggests that a compound that has the ability to protect mitochondrial function (as assessed by several in vitro tests) will have some ability to protect cells from damage from ischemia and reperfusion. The results reported are that all thiols tested, at least partially, recouple FCCP-uncoupled mitochondria and that most thiols tested including MPG and bucillamine, protect mitochondrial function from aging. However, in the apparently key experiment to assess utility of the test compounds for improvement of damaged heart function, the assessment of increased aortic flow in a working rat heart preparation, MPG and its oxidized dimer were found to significantly enhance aortic flow, while bucillamine and a number of other thiols display negligible effect. This reference suggests that MPG, not thiols in general and not bucillamine, will have a therapeutic utility for treatment of reperfusion damage.

Contrary to the reports of the prior art, this invention demonstrates that bucillamine, its homolog Compound A and structurally related N-mercaptoalkanoylcysteines, are highly effective for protecting cultured cardiac myoctes against oxidant injury and are, in fact, about twice as effective in this assay compared to MPG.

SUMMARY OF THE INVENTION

This invention provides a method for treatment of ischemic diseases such as myocardial infarction, cerebral infarction, and related diseases such as heart failure and atherosclerosis and other conditions involving injury to mammalian tissue by reactive oxygen species. The methods of treatment of this invention involve the administration of a pharmaceutically effective amount of a N-mercaptoalkanoylcysteine derivatives of formula I:

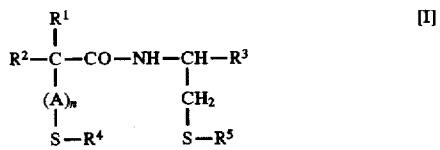

or a pharmaceutically acceptable salt thereof together with a pharmaceutically acceptable carrier to a mammal exhibiting symptoms of the disease or disorder. In formula I, $R^1$ and $R^2$, independently of one another, can be alkyl groups, particularly lower alkyl groups; $R^3$ can be a carboxyl group or an ester or amide thereof; $R^4$ or $R^5$, independently of one another, are selected from the group consisting of a hydrogen atom, an alkyl group, an alkanoyl group, a phenyl-alkyl group or a phenylcarbonyl group, and the phenyl ring in the phenyl-alkyl and phenylcarbonyl groups can be substituted by at least one selected from halogen atoms, and alkyl, hydroxy, alkoxy, alkylenedioxy, nitro, amino and alkylamino groups; n is an integer that is 0 or 1; and "A" is a lower alkylene group, such as a —$CH_2$— group. For all R groups of formula I that contain alkyl, alkenyl, phenyl-alkyl, alkanoyl, alkoxy, alkylenedioxy or alkylamino groups, preferred groups are those that contain from 1 to about 6 carbon atoms (i.e., lower alkyl).

Preferred N-mercaptoalkanoylcysteine derivatives are those which exhibit an enhanced pharmaceutical effect, substantially greater than that exhibited by MPG, for prevention of cell injury due to reactive oxygen species which are produced during reperfusion of ischemic organs. Preferred N-mercapto-alkanoylcysteine derivatives are those in which $R^1$ and $R^2$ are lower alkyl (having from 1 to about 6 carbon atoms); those in which $R^4$ and $R^5$ are hydrogen or methyl groups; those in which A is —$CH_2$—. More preferred N-mercaptoalkanoylcysteine derivatives useful for treatment of ischemic diseases are bucillamine and Compound A.

The invention is also directed to a method of protecting live mammalian tissue from injury resulting from exposure to reactive oxygen species formed after reestablishment of blood flow to a body organ after restriction of blood flow to that organ. It comprises administration of a compound of formula I or a pharmaceutically acceptable salt thereof along with pharmaceutically acceptable carriers. Preferred compounds of formula I in this method are bucillamine and Compound A.

This invention is further directed to the use of compounds of this invention of formula I for the preservation of mammalian organs, organ tissue or other tissue during transplantation procedures. An amount of the compound effective for preservation of the organ or tissue is included in the preservation solution in which the organ or tissue is contacted during transplantation.

The pH in water of certain of the compounds of this invention is acidic so that it may be necessary to neutralize aqueous solutions with a base such as NaOH to preferably achieve physiologic pH.

The compounds of this invention can be easily administered either orally or parenterally as appropriate for treatment of a given ischemic disorder. They can be readily administered, for example, at the time of reperfusion to rapidly neutralize the damaging effects of reactive oxygen species.

DETAILED DESCRIPTION OF THE INVENTION

Definitions

Figure 1:
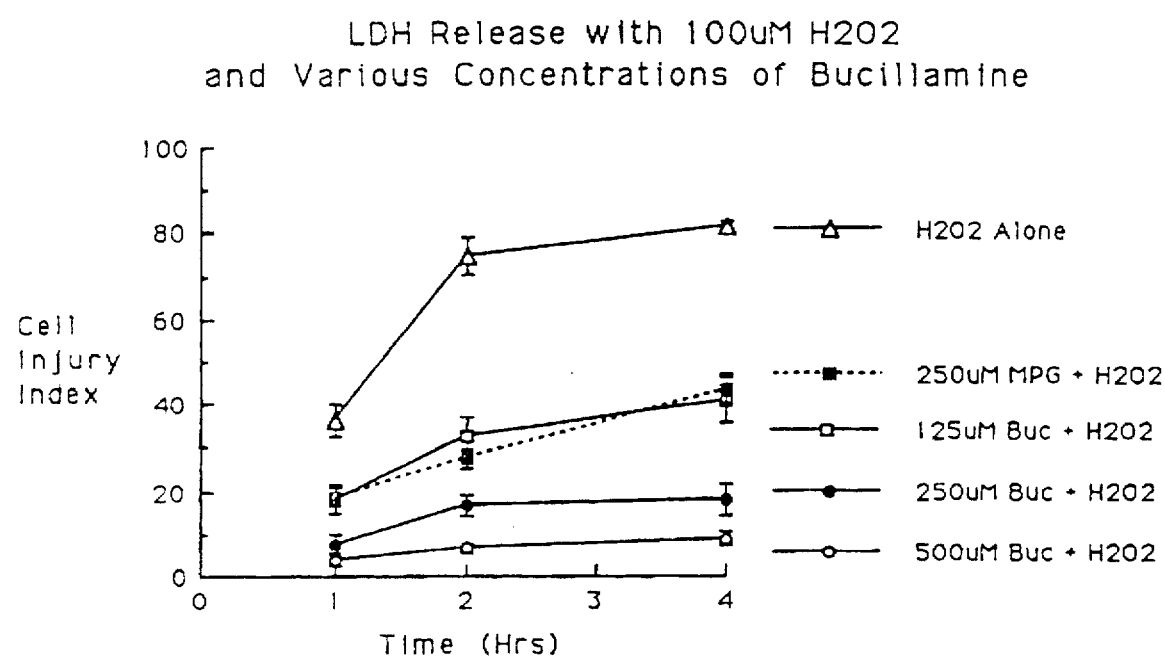
FIG. 1 is a graph of Cell Injury Index as a function of time for exposure to 100 µM $H_2O_2$ and various concentrations of BUC bucillamine (and one concentration of MPG). Cell injury index reflects release of lactate dehydrogenase (LDH) from injured cells. Results shown are for $H_2O_2$ alone (solid line, open triangles); 250 µM MPG+$H_2O_2$ (dashed line, solid squares); 125 µM Buc+$H_2O_2$ (solid line, open squares); 250 µM Buc+$H_2O_2$ (solid line, closed circles); 500 µM Buc+$H_2O_2$ (solid line, open circles). These results were obtained when cultured adult rat cardiac myocytes were exposed to $H_2O_2$ for 4 hours with or without simultaneous treatment with bucillamine or MPG. Both MPG and bucillamine reduced Cell Injury Index, but bucillamine was approximately twice as effective on an equimolar basis compared with MPG.

The following terms used herein are defined:

The term "alkyl group" takes its standard meaning to indicate a linear or branched alkyl group. The term lower alkyl group indicates alkyl groups having from 1 to about 6 carbon atoms and includes for example methyl, ethyl, propyl, pentyl, hexyl, isopropyl, isobutyl, isopentyl, isohexyl, t-butyl and t-pentyl groups. More preferred lower alkyl groups are methyl and ethyl groups.

The term "alkoxy group" takes its standard meaning to indicate a linear or branched alkoxy group. The term lower alkoxy indicates alkoxy groups having from 1 to about 6 carbon atoms and includes for example methoxy, ethoxy, propoxy, pentoxy, hexlyoxy, isopropoxy, isobutoxy, isopentoxy, isohexyloxy, t-butoxy and t-pentoxy, groups. More preferred lower alkoxy groups are methoxy and ethoxy groups.

The terms "alkanoyl", "alkylene", and "alkylenedioxy" take their standard meaning in the art. When these terms are modified by the word "lower" they refer to linear or branched groups having from 1 or 2 (as appropriate for the particular group) up to about 6 carbon atoms. Alkylenedioxy groups have a linear or branched alkylene group between two oxygen atoms. Exemplary alkanoyl groups include: acetyl, propionyl, butyryl, valeryl, pivaloyl, among others. The more preferred alkanoyl group is acetyl. Exemplary alkenyl groups include, methylene, ethylene, trimethylene, hexamethylene, propylene, (ethyl)methylene, and (dimethyl)methylene groups. Exemplary alkylenedioxy groups include: methylenedioxy, ethylenedioxy, propylenedioxy, and (diethyl)methylenedioxy.

The term "phenyl-alkyl" refers to a group containing a phenyl and a linear or branched alkyl group. The group may be attached to the core via the alkyl group, such as in a benzyl group or the phenyl group, such as in a (4-methyl) phenyl group. The phenyl ring in the phenyl alkyl group can be substituted by at least one group selected from the group of halogen atoms (F, Cl, or I) lower alkyl, hydroxy, lower alkoxy, lower alkylenedioxy, nitro, amino, and lower alkylamino.

The terms "ester" or "amide" refer to ordinary esters or amides of carboxylic acids. Lower alkyl esters include methyl esters, ethyl esters, isopropyl esters, butyl esters and hexyl esters. Esters include phenyl-alkyl esters, such as benzyl esters. Amides include amides with ammonia; lower alkyl amines either primary or secondary amines, such as methyl amine, diethyl amine, ethyl amine, diethyl amine; and amides with phenyl-alkylamines, such as benzylamine. Preferred esters are methyl, ethyl or benzyl esters. Preferred amides are amides with ammonia or amides with methyl amine, dimethyl amine, ethyl amine or diethyl amine.

Pharmaceutically acceptable salts of the compounds of this invention are those acceptable for use in medicines administered to mammals or humans. They include, among many others, salts with alkali metals or alkaline earth metals; ammonium salts; and salts with organic amines such as diethylamine or triethanolamine.

The compounds of this invention include diastereomers and optical isomers of the compound whose formulas are specifically provided. The invention also includes the compounds specifically described in the form of their hydrates.

The clinical utility of the administration of the N-mercaptoalkanoylcysteine derivatives described above was demonstrated by application to adult rat cardiac myocytes. A method has been reported for determining the degree of cell damage in cardiac muscle due to exposure to reactive oxygen species by measuring the amount of lactate dehydrogenase released from cultured myocardial cells [see Am. J. Physiol., 266:H121–H127 (1994)]. The amount of lactate dehydrogenase released is quantitated by measurement of the activity of this enzyme in the medium in wells in which cultured myocardial cells are grown. In this manner damage can be assessed by either the addition of hydrogen peroxide to wells containing cultured myocardial cells or by adding a mixture of xanthine and xanthine oxidase which is employed for production of hydrogen peroxide and superoxide radical in the wells. Using this method in cultured myocardial cells the compounds of the invention are tested to determine whether they prevent or reduce the cell-damaging effects of exposure to hydrogen peroxide alone or of exposure to xanthine and xanthine oxidase, for production of hydrogen peroxide and superoxide radical.

Method for Assessing Test Compounds for Utility in the Treatment of Ischemic Disorders and Protection form Reactive Oxygen Species The thorax of a male rat was cut open. Calcium free, modified Krebs Ringer buffer solution that had been cooled with ice in water was introduced into the thoracic cavity, and the heart together with a contiguous portion of the aorta was excised. The aorta was then cannulated for perfusion of the heart by the noncirculating Langendorf technique using collagenase and hyaluronidase in a modified Krebs Ringer buffer solution containing 50 µM $Ca^{2+}$, which was at 37° C. and gassed with oxygen and 5% carbon dioxide. The ventricles were then separated and cut into small pieces which were incubated in collagenase and trypsin in a modified Krebs Ringer buffer solution containing 50 µM $Ca^{2+}$, which was at 37° C. and gassed with oxygen and 5% carbon dioxide. The tissue was then triturated after which a trypsin inhibitor at 4° C. was added to digest the tissue. The digested tissue was then filtered and centrifuged. The cell pellet was then suspended in a modified Krebs Ringer buffer solution containing 500 µM $Ca^{2+}$. To remove damaged cells and gradually increase $Ca^{2+}$, three gravity sedimentations were done in 500 µM, 1 mM, and 1.4 mM $Ca^{2+}$ at 37° C. The cells were then suspended in tissue culture medium containing 5% fetal calf serum and 1.4 mM Ca++ in 17 mm diameter wells.

The cells were cultured for 48 hours, after which they were washed and modified Krebs Ringer buffer solution containing 5% fetal calf serum and 1.4 mM Ca in 17 mm diameter wells was again added to the wells. In test wells either 100 mM reagent grade hydrogen peroxide or a mixture of xanthine 400 mM and xanthine oxidase 8.8 mU was added with or without a test compound. Wells to which none of these agents were added served as "controls." In other wells a detergent, polyoxyethylene (10) octyphenyl ether, which causes lysis of all cells, was added.

The degree of cell damage was measured as a cell injury index (CII) calculated according to the following equation:

$$CII(\%) = [(A-B)/(C-B)] \times 100$$

where "A" is the lactate dehydrogenase activity in the medium in the test wells; "B" is the lactate dehydrogenase activity in the medium in the "control" wells; and "C" is the lactate dehydrogenase activity in the medium in the wells containing polyoxyethylene (10) oxtyphenyl ether.

Using the methods described above, the lactate dehydrogenase release from the cultured myocardial cells can be determined for specified treatment conditions for various periods of time, the corresponding CII value determined and the individual results calculated at each time period.

Results

Examples of the usefulness of the test compounds are shown below with the results summarized in Tables 1 and 2. Table 1 shows the cell-protective effect of bucillamine or Compound A on myocardial cells exposed to hydrogen peroxide and Table 2 shows the protective effect of bucillamine on myocardial cells exposed to hydrogen peroxide and superoxide radical generated by xanthine/xanthine oxidase.

Each result shown in Table 1 represents a mean value from two experiments performed in triplicate (n=6 wells).

Exposure to hydrogen peroxide without either test compound present resulted in a CII of 81.6% at the end of 4 hours and lesser degrees of injury at 1 or 2 hours. However, addition of either bucillamine or Compound A markedly reduced the CII at 4 hours and also reduced CII at exposure times of 1 or 2 hours. The degree of protection afforded by bucillamine or Compound A depended upon the concentration of the compound added. This verifies that bucillamine or Compound A inhibited the release of lactate dehydrogenase from cultured myocardial cells due to injury caused by exposure to hydrogen peroxide.

TABLE 1

|  | Degree of Cell Damage (%) | | |
| --- | --- | --- | --- |
|  | 1 hour | 2 hours | 4 hours |
| No test compound present | 36.5 | 74.7 | 81.6 |
| Bucillamine 125 µM | 17.8 | 32.6 | 41.0 |
| 250 µM | 7.6 | 16.9 | 17.9 |
| 500 µM | 3.9 | 6.6 | 8.8 |
| Compound A 125 µM | 25.1 | 31.6 | 40.1 |
| 250 µM | 10.6 | 16.9 | 20.2 |
| 500 µM | 9.1 | 11.0 | 13.8 |

TABLE 2

|  | Degree of Cell Damage (%) | | |
| --- | --- | --- | --- |
|  | 1 hour | 2 hours | 4 hours |
| No test compound present | 0.7 | 10.3 | 62.1 |
| Bucillamine 125 µM | 1.0 | 0.3 | 17.6 |
| 250 µM | 0.9 | −1.5 | 4.3 |

Each result in Table 2 is the mean value from experiments which were performed in triplicate on three separate occasions (n=9 wells). When no test compound was present, exposure to xanthine/xanthine oxidase resulted in substantial cell damage (CII 62.1%) after 4 hours but little damage earlier. When bucillamine was added, the degree of cell damage at 4 hours of exposure to xanthine/xanthine oxidase was lowered substantially. The degree of protection depended upon the concentration of bucillamine. This verifies that bucillamine inhibited the release of lactate dehydrogenase from cultured myocardial cells due to injury caused by exposure to xanthine/xanthine oxidase, which causes generation of hydrogen peroxide and superoxide radical.

As has been demonstrated in the two examples above, the test compounds prevent myocardial cell damage caused by exposure to reactive oxygen species. Reactive oxygen species are produced when hearts or other organs are reperfused after transient ischemia.

The compounds of this invention can inhibit the release of lactate dehydrogenase from cultured myocardial cells due to injury caused by exposure to xanthine/xanthine oxidase, which causes generation of hydrogen peroxide and superoxide radical. The compounds of this invention are useful for treatment of myocardial infarctions, cerebral infarctions or other conditions in which an interruption of blood flow to an organ is treated by reperfusion. They are also useful for prevention of forms of vascular injury in which reactive oxygen species are involved, including exposure to ischemia and reperfusion and development of atherosclerosis. Because there is evidence that reactive oxygen species are a cause of heart failure, independently of the presence of ischemia and reperfusion, the compounds of this invention are also useful for the prevention or treatment of this condition. Because there is evidence that generation of superoxide radical or other reactive oxygen species cause tolerance to nitroglycerine and related compounds, the compounds of this invention are also useful for the prevention or treatment of this condition.

Figure 2:
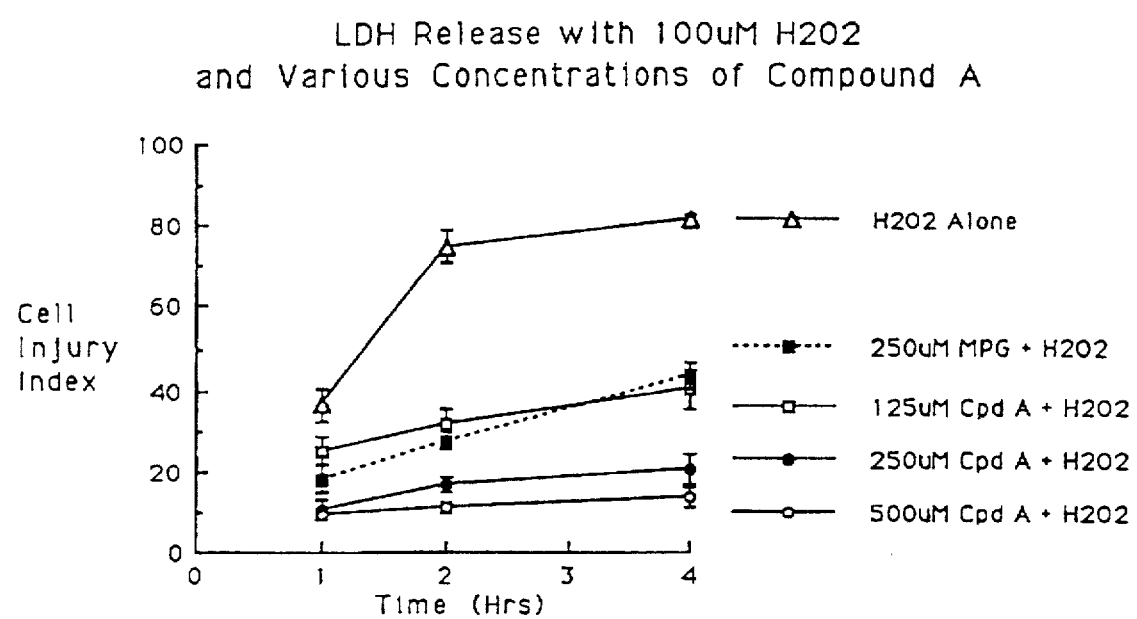
FIG. 2 is a graph of Cell Injury Index as a function of time for exposure to 100 µM $H_2O_2$ with various concentrations of compound A (CpdA) or MPG. Cell Injury Index reflects release of LDH from injured cells. Results shown are for $H_2O_2$ alone (solid line, open triangles); 250 µM MPG+$H_2O_2$ (dashed line, solid squares); 125 µM CpdA+$H_2O_2$ (solid line, open squares); 250 µM CpdA +$H_2O_2$ (solid line, closed circles); 500 µM CpdA+$H_2O_2$ (solid line, open circles). Cultured adult rat cardiac myocytes were exposed to $H_2O_2$ for 4 hours with or without treatment with CpdA or MPG. Both MPG and CpdA reduce Cell Injury Index, but CpdA was approximately twice as effective on an equimolar basis compared with MPG.

Certain compounds of this invention have been demonstrated in the test method described above to be significantly more effective than MPG in preventing cell injury. Exemplary results are shown in FIGS. 1 and 2 for bucillamine and Compound A, respectively, compared to MPG, employing a cell injury index based on release of LDH from cells damaged by $H_2O_2$. These results indicate that both bucillamine and Compound A are about twice as effective (on a weight basis) as MPG.

The ability of compounds to prevent injury by hydrogen peroxide or other reactive oxygen species in cultured cardiac myocytes is predictive of the ability of these compounds to prevent reperfusion injury in intact hearts in animals. For example, dimethylthiourea and MPG were effective in preventing injury due to hydrogen peroxide in cultured cardiac myocytes [Am. J. Physiol (1994) 266:H121–H127] and both were also effective in reducing myocardial infarct size in canine hearts exposed to ischemia and reperfusion [Circ. Res. (1991) 68:1652–1659); Circulation (1994) 89:1792–1801].

The compounds of this invention are commercially available or can be prepared by well known techniques from readily available starting materials. U.S. Pat. Nos. 4,305,958 and 5,292,926 provide details of the preparation of these compounds.

The compounds of this invention can be administered either orally or parenterally. Oral dosage forms of the compounds of the invention include tablets, capsules, granules, powders, etc., all of which can be readily prepared by known techniques. Oral dosage forms can be formulated optionally with vehicles, lubricants, binders, disintegrators and coating agents, all appropriately chosen for the particular application. Parenteral dosage forms are prepared using known techniques with appropriate buffered vehicles. Dosage of the compounds of this invention can be determined as is understood in the art depending on the condition and age of the patient and the dosage form chosen.

While the invention has been described in detail and with reference to specific embodiments thereof, it will be apparent to one skilled in the art that various changes and modifications can be made without departing from its spirit and scope. All of the references cited herein are incorporated by reference in their entirety herein. These references provide among other things details of assays and sources of compounds of this invention.

What is claimed is:

1. A method for preserving organs or other tissue for transplantation which comprises administration to the organ or tissue of a preservation solution which comprises an amount of a compound of formula I or a pharmaceutically acceptable salt thereof effective for organ preservation:

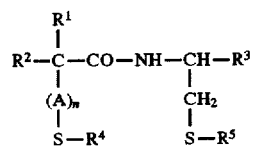

wherein:

$R^1$ and $R^2$, independently of one another, are lower alkyl groups;

$R^3$ is a carboxyl group which can be converted into an ester or amide;

$R^4$ is selected from the group consisting of a hydrogen atom, a lower alkyl group, a lower alkanoyl group, a phenyl-lower alkyl group or a phenylcarbonyl group, and the phenyl ring in the phenyl-lower alkyl and phenylcarbonyl groups can be substituted by at least one selected from halogen atoms, and lower alkyl, hydroxy, lower alkoxy, lower alkylenedioxy, nitro, amino and lower alkylamino groups;

$R^5$ represents a hydrogen atom, a lower alkyl group, a lower alkanoyl group, a phenyl-lower alkyl group or a phenylcarbonyl group, and the phenyl ring in the phenyl-lower alkyl and phenylcarbonyl groups can be substituted by at least one selected from halogen atoms, and lower alkyl, hydroxy, lower alkoxy, lower alkylenedioxy, nitro, amino and lower alkylamino groups;

"n" is an integer that is 0 or 1; and

"A" is a lower alkylene group.

2. The method of claim 1 wherein in the compound of formula I $R^3$ represents a carboxyl group which can be converted into a lower alkyl or phenyl-lower alkyl ester, or represents a carboxyl group which can be converted into an amide with ammonia, a lower alkylamine or a phenyl-lower alkylamine; and the phenyl ring in the phenyl-lower alkyl group and the phenyl-lower alkylamine can be substituted by at least one selected from halogen atoms, and lower alkyl, hydroxy, lower alkoxy, lower alkylenedioxy, nitro, amino and lower alkylamino groups.

3. The method of claim 2 wherein in the compound of formula I $R^3$ is a carboxyl group and $R^4$ and $R^5$ are hydrogen atoms.

4. The method of claim 3 wherein in the compound of formula I $R^1$ and $R^2$ are both methyl groups and A is a —$CH_2$—.

5. The method of claim 1 wherein in the compound of formula I $R^1$ and $R^2$ are lower alkyl groups; $R^4$ and $R^5$, independently of one another, are hydrogen atoms or methyl groups and A is a —$CH_2$— group.

6. The method of claim 1 wherein the compound of formula I is bucillamine.

7. The method of claim 1 wherein the compound of formula I is N-2,2-dimethyl-2-mercaptopropionyl)-L-cysteine.

8. The method of claim 1 wherein $R^4$ is selected from the group consisting of a hydrogen atom, a lower alkyl group and a lower alkanoyl group.

9. The method of claim 1 wherein $R^5$ is selected from the group consisting of a hydrogen atom, a lower alkyl group and a lower alkanoyl group.

10. The method of claim 2 wherein $R^3$ is an ester.

11. The method of claim 2 wherein $R^3$ is an amide.

12. The method of claim 1 wherein said organ or other tissue for transplant to be preserved is a heart, a kidney, a lung or lung tissue, or a liver or liver tissue.

* * * * *

UNITED STATES PATENT AND TRADEMARK OFFICE
CERTIFICATE OF CORRECTION

PATENT NO. : 5,756,547

DATED : May 26, 1998

INVENTOR(S) : Horwitz

It is certified that error appears in the above-identified patent and that said Letters Patent is hereby corrected as shown below:

On the title page item [54], delete the title and replace it with --METHOD OF PRESERVING ORGANS OR TISSUE FOR TRANSPLANTATION--.

Signed and Sealed this

Thirtieth Day of March, 1999

Attest:

Q. TODD DICKINSON

*Attesting Officer*   *Acting Commissioner of Patents and Trademarks*